United States Patent [19]

Tweedle et al.

[11] Patent Number: 5,262,532
[45] Date of Patent: Nov. 16, 1993

[54] PARAMAGNETIC METALLOPORPHYRINS AS CONTRAST AGENTS FOR MAGNETIC RESONANCE IMAGING

[75] Inventors: Michael F. Tweedle, Princeton, N.J.; Lon J. Wilson, Tex.; Joseph E. Bradshaw, both of Houston, Tex.; Daniel W. Lee, Lake Jackson, Tex.

[73] Assignee: E.R. Squibb & Sons, Inc., Princeton, N.J.

[21] Appl. No.: 733,568

[22] Filed: Jul. 22, 1991

[51] Int. Cl.$^5$ .................................... C07D 487/22
[52] U.S. Cl. ............................ 540/145; 424/9
[58] Field of Search ................ 540/145; 514/410

[56] References Cited

U.S. PATENT DOCUMENTS

| | | | |
|---|---|---|---|
| 2,005,511 | 12/1932 | Stoll et al. | 540/145 |
| 2,740,794 | 4/1956 | Bonner et al. | 540/145 |
| 4,728,575 | 3/1988 | Gamble et al. | 428/402.2 |
| 4,804,529 | 2/1989 | Bardy et al. | 424/9 |
| 4,986,256 | 6/1991 | Cohen et al. | 128/653.4 |
| 4,992,257 | 2/1991 | Bonnett et al. | 424/9 |

FOREIGN PATENT DOCUMENTS

| | | | |
|---|---|---|---|
| 0118913 | 3/1983 | European Pat. Off. | 540/145 |
| 0355041 | 2/1990 | European Pat. Off. | |
| 3809671 | 9/1989 | Fed. Rep. of Germany | |

OTHER PUBLICATIONS

"Porphrins and Metalloporphyrins" by J. E. Falk Elsevier Publishing Company (1964) pp. 30–31 and 41–49.
P. Hambright et al., "The Distribution of Various Water Soluble Radioactive Metalloporphyrins in Tumor Bearing Mice", Bioinorg. Chem. 5, 87–92 (1975).
N. J. Patronas et al., "Metalloporphyrin Contrast Agents for Magnetic Resonance Imaging of Human Tumors in Mice", Cancer Treatment Reports 70, 391–395 (1986).
C. Chen et al., "Paramagnetic Metalloporphyrins as Potential Contrast Agents in NMR Imaging", FEBS Letters 168, 70–73 (1984).
L. J. Boucher, "Manganese Porphyrin Complexes", Coord. Chem. Rev., 289–329, (1972).
S. H. Koenig et al., "The Anomalous Relaxivity of $Mn^{3+}(TPPS_4)$", Magnetic Resonance in Medicine 4, 252–260 (1987).

*Primary Examiner*—Thurman K. Page
*Assistant Examiner*—Jyothsna Venkat
*Attorney, Agent, or Firm*—Ellen K. Park

[57] ABSTRACT

Porphyrin-complex compounds useful as contrast agents in magnetic resonance imaging (MRI) having the formula

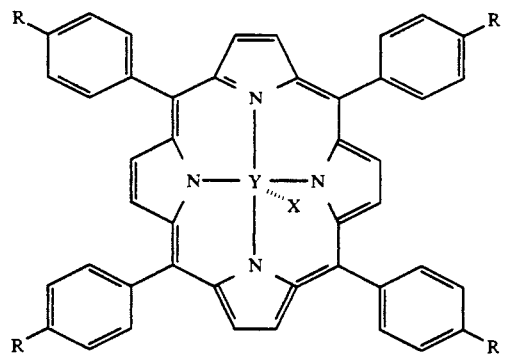

where Y is a transition metal such as $Fe^{III}$, $Cr^{III}$, $Mn^{III}$, $Mn^{II}$ and $Cu^{II}$, X is a biologically well-tolerated metal complexing anion such as $Cl^-$, $CF_3SO_3$ or $CF_3COO^-$ and R is a nonionic water solubilizing moiety.

3 Claims, 3 Drawing Sheets

PARAMAGNETIC METALLOPORPHYRINS AS CONTRAST AGENTS FOR MAGNETIC RESONANCE IMAGING

FIELD OF INVENTION

This invention relates to magnetic resonance imaging (MRI) and more particularly to new porphyrin-complex compounds, useful as contrast agents in MRI.

BACKGROUND OF THE INVENTION

Magnetic resonance imaging is a valuable aid in diagnosing and locating diseased tissue. Certain paramagnetic metal ions influence the MRI images in favorable ways; however, the inherent toxicity of metal ions has hampered their use as contrast agents. Therefore, chelating agents are used to complex the metal ions, producing in some, but not all cases, well tolerated metal chelate compounds.

Porphyrins have been used as chelating agents for paramagnetic metal ions to achieve higher contrast in MRI images of neoplastic tissue. However, the metalloporphyrins used are made water soluble by several (usually four) highly acidic or basic groups on the periphery of the porphyrin ligand. These groups carry dissociable counter ions, which when the metalloporphyrins are dissolved, dissociate and greatly increase the osmolality of the resulting solutions. Elevated osmolality causes discomfort and has been linked to adverse toxic drug reactions in humans.

Desired properties for contrast agents used in MRI include but are not limited to high water solubility, low osmolality and high relaxivity. Relaxivity is a measure of the effectiveness of each metal chelate complex in affecting $T_1$ and $T_2$ relaxation times. The greater the relaxivity, in general, the more effective is the metal complex as a contrast agent. The results of relaxivity studies on manganese porphyrins are disclosed in Chi-wan Chen et al., FEBS Lett., 168, 70 (1984) and Seymour H. Koening et al., Magn. Reson. Med., 4, 252, (1987); these references indicate that these compounds have anomalously high relaxivities.

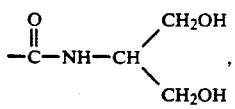

Y is Mn and X is Cl$^-$.

Figure 3:
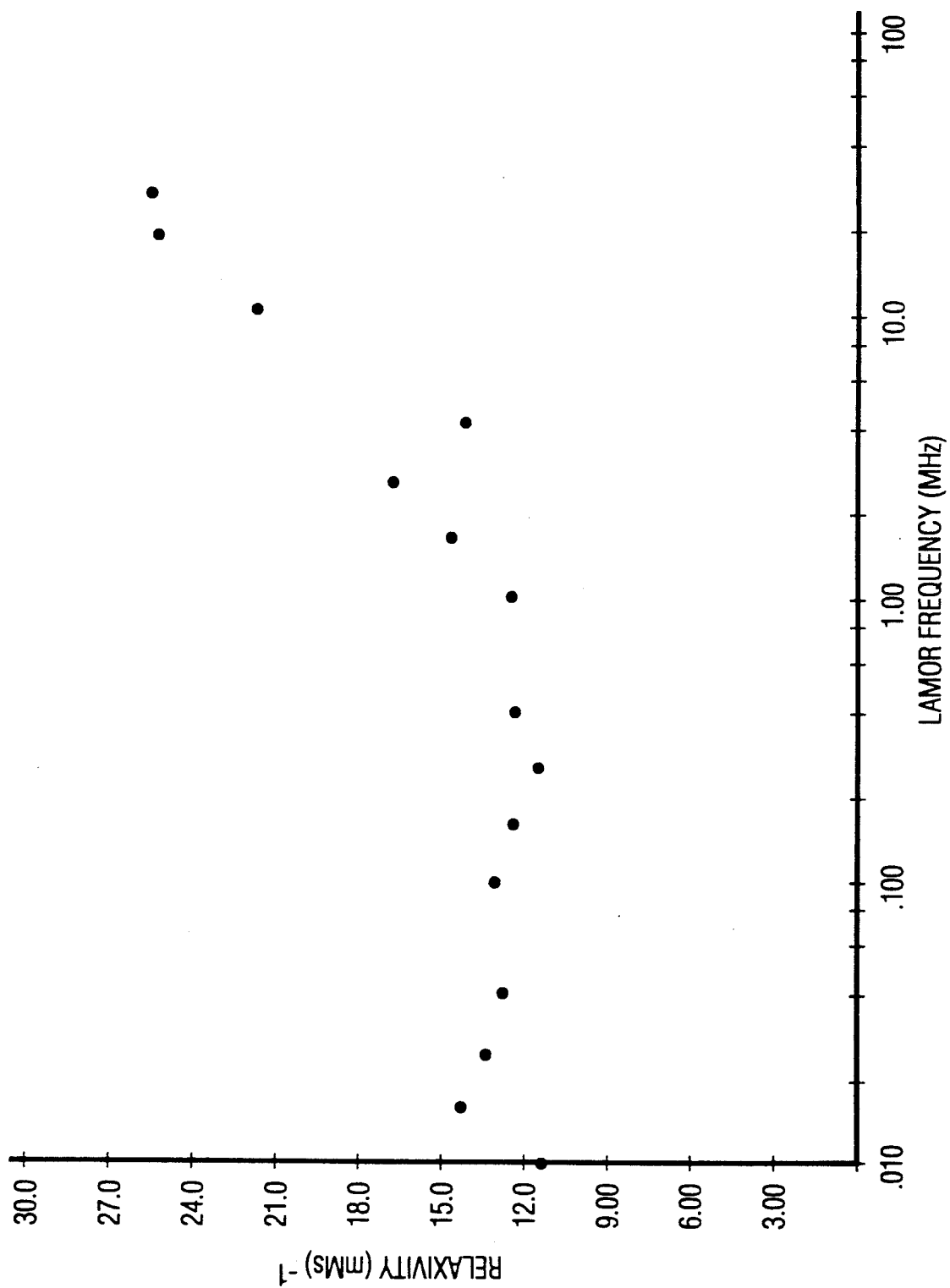

FIG. 3 is a graph of the relaxivity vs. frequency of the compound of formula I where R is

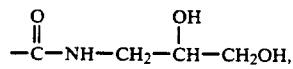

Y is Mn and X is Cl$^-$.

BRIEF DESCRIPTION OF THE INVENTION

The invention comprises compounds having the following structure:

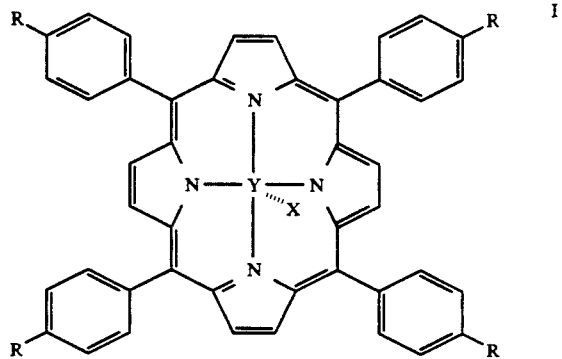

where Y is a transition metal such as Fe$^{III}$, Cr$^{III}$, Mn$^{III}$, Mn$^{II}$ and Cu$^{II}$, where Mn$^{III}$ is preferred; X is a biologically well-tolerated metal complexing anion such as Cl$^-$, CF$_3$SO$_3^-$ or CF$_3$COO$^-$; R is a nonionic water solubilizing moiety such as hydroxy, methoxy and those disclosed in G. B. Hoey & H. R. Smith, "Chemistry of X-Ray Contrast Media", *Radiocontrast Agents* (M. Sovak), pp 23-125, Springer-Verlag Berlin Heidelberg New York Tokyo (1984). Preferred R groups are

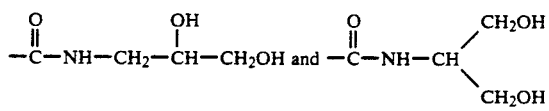

and pharmaceutically acceptable salts thereof.

Compounds having the above structures are believed to function well as MRI agents. It has been found that the preferred compounds are highly water soluble, with low osmolality and surprisingly high relaxivities.

DETAILED DESCRIPTION OF THE INVENTION

In its broadest aspects, the present invention relates to the compounds of formula I, to pharmaceutical media containing these compounds and their use in diagnostics and therapy.

The following definitions apply throughout this specification, unless otherwise limited in specific instances.

The term "transition metal" means any of those elements that have incompletely filled d subshells or give rise readily to cations that have incompletely filled d subshells and includes elements of atomic number 21-30, 39-48 and 57-80.

The term "biologically well-tolerated metal complexing anion" means any negatively charged ion which is known not to increase the toxicity of given compounds which has tolerance as great or greater than the metal chelate, and which bonds to the metal of the metal chelate.

The term "nonionic water solubilizing moiety" means one or more functional groups which allow for water solubility that do not form ionic species when dissolved in water.

The term "amino sugars" means any compound or functional group that is normally classified as sugars with the amine (—N(R$_1$)$_2$, where R$_1$ is independently H or a lower alkyl) functionality incorporated within them.

Lower alkyl as used herein includes straight or branched chain saturated hydrocarbons having up to 6 carbon atoms.

The term "poly alcohol amines" means compounds or functionalities that contain two or more alcohol (—OH) substituents along with one amine substituent.

The term "inorganic acid halides" means any of a group of halogenated inorganic compounds used to convert carboxylic acid functionalities to acyl or aryl halides. These may include but are not limited to oxalyl chloride and/or bromide, $SOX_2$, $PX_2$, $PX_5$, where X represents a halogen.

Solvents having "acceptable solubility compatibility" are those solvents in which each of the reactants is soluble and also does not interfere with the desired reaction.

"Appropriately substituted pyrroles" are those pyrroles which are unsubstituted or may be substituted at the 3 and/or 4 positions, and are not substituted in the 2 and 5 positions, with functionalities that do not hinder water solubility. Examples of such pyrroles include those that are substituted with methyl, methoxy or ethoxy.

To prepare the compounds of formula I, a compound of the formula

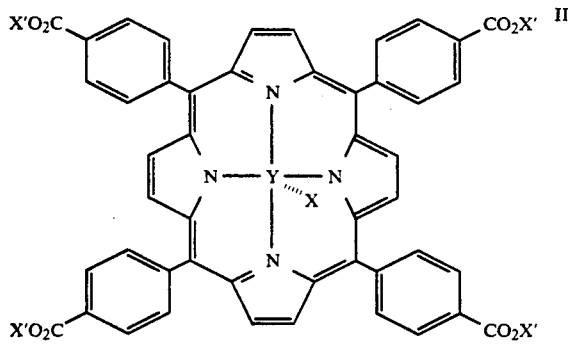

is reacted with compounds having nonionic water solubilizing moieties such as various amino sugars or poly alcohol amines, such as 3-amino-1,2-propanedio; 2-amino-1,3-propanediol; or 2-amino-2-(hydroxymethyl)-1,3-propanediol in a solvent in which all the reactants are soluble, such as methanol, where X and Y have been hereinbefore defined, and X' is a halogen such as $Cl^-$.

Compounds of formula II may be prepared by reacting compounds of formula

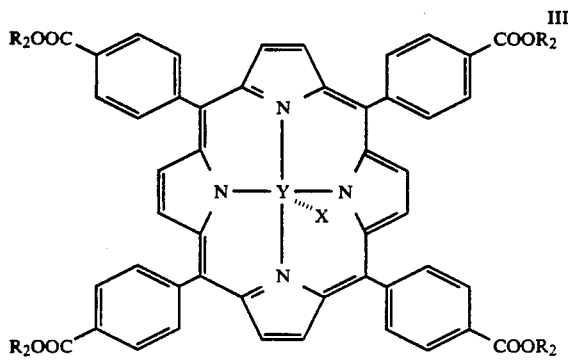

where X and Y have been hereinbefore defined and $R_2$ is an appropriate leaving group functionality such as H; with inorganic acid halides (acyl halides) such as thionyl chloride in an appropriate dry, degassed solvent such as dimethylformamide.

Compounds of formula III may be prepared by reacting compounds of formula

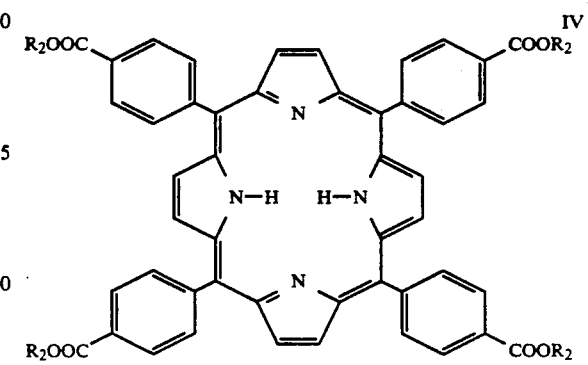

with a hydrated metal ion complex having the formula $YX_n$, where X and Y are as defined previously and $n=2$ or 3, such as $MnCl_2 \cdot 4H_2O$ in the presence of a solvent with acceptable solubility compatibility such as dimethylformamide where $R_2$ has been hereinbefore defined.

Compounds of formula IV may be prepared by reacting appropriately substituted pyrroles with aldehydes with an accessible carboxylate group such as 4-carboxybenzaldehyde in proton-donating, relatively weak acids such as propionic acid.

The following examples and preparations describe the manner and process of making and using the invention and are illustrative rather than limiting. It should be understood that there may be other embodiments which fall within the spirit and scope of the invention as defined by the claim appended hereto.

EXAMPLE 1

Managanese(III)5,10,15,20-tetrakis[[4-carboxylic acid-(1,3-dihydroxyisopropyl)amide]phenyl]-porphyrin chloride

A. 5,10,15,20-tetrakis(4-carboxyphenyl)porphyrin

The acid derivative of 5,10,15,20-tetrakis(phenyl)porphyrin was prepared according to the procedure of Longo, et al. J. Heterocyclic Chem., 6, 927 (1969). 1.50 g 4-Carboxy-benzaldehyde (0.01 mole) and 0.69 mL pyrrole (0.01 mole) were combined in 150 mL propionic acid. The mixture was refluxed for 2 to 4 hours, cooled to room temperature, and then filtered through a fine frit. The resulting solid was then extracted into methanol and filtered through a medium frit. The filtrate was placed in a round-bottom flask, and the methanol removed on a rotary evaporator, leaving a solid purple residue. The recovered solid was then dried overnight under vacuum.

Yield: 0.83 g.; 42%.

Formulation: 5,10,15,20-tetrakis(4-carboxyphenyl)porphyrin.$CH_3OH$.$C_{49}H_{34}N_4O_9$ Proposed: %C 71.53, %H 4.16, %N 6.32

Found: %C 71.49, %H 4.04, %N 6.36

B. Manganese(III)5,10,15,20-tetrakis(4-carboxyphenyl)-porphyrin chloride

The metallation of the three porphyrin was accomplished via a modified procedure of Adler, et al., J. Inorg. Nucl. Chem., 2443, (1970). Originally, a 10:1 molar ratio of $MnCl_2.4H_2O$ to the title A compound was employed as in Adler's work, with consistently poor elemental analyses resulting from this protocol. Therefore, a 1:1 molar ratio of starting materials was used. The title A compound (0.75 g; $9.48 \times 10^{-4}$ moles) and 0.188 g $MnCl_24H_2O$ ($9.48 \times 10^{-4}$ moles) were combined in 150 mL dimethylformamide. The resulting mixture was refluxed overnight, the dimethylformamide removed under reduced pressure, and the crude solid dried on the vacuum line. The solid was then taken up into methanol, filtered, and the filtrate combined with an equal volume of water. The mixture was reduced in volume under reduced pressure by approximately 50% and then filtered through a medium frit. The dark solid collected was dried overnight on the vacuum line.

Yield: 0.38 g; 46%.

Formulation: Manganese(III)5,10,15,20-tetrakis(4-carboxyphenyl)porphyrin chloride.$C_3$ $H_7NO.2H_2O.C_{51}H_{39}N_{11}MnCl$ Proposed: %C 61.98, %H 3.98, %N 7.09

Found: %C 62.09, %H 3.97, %N 7.05.

Figure 1:
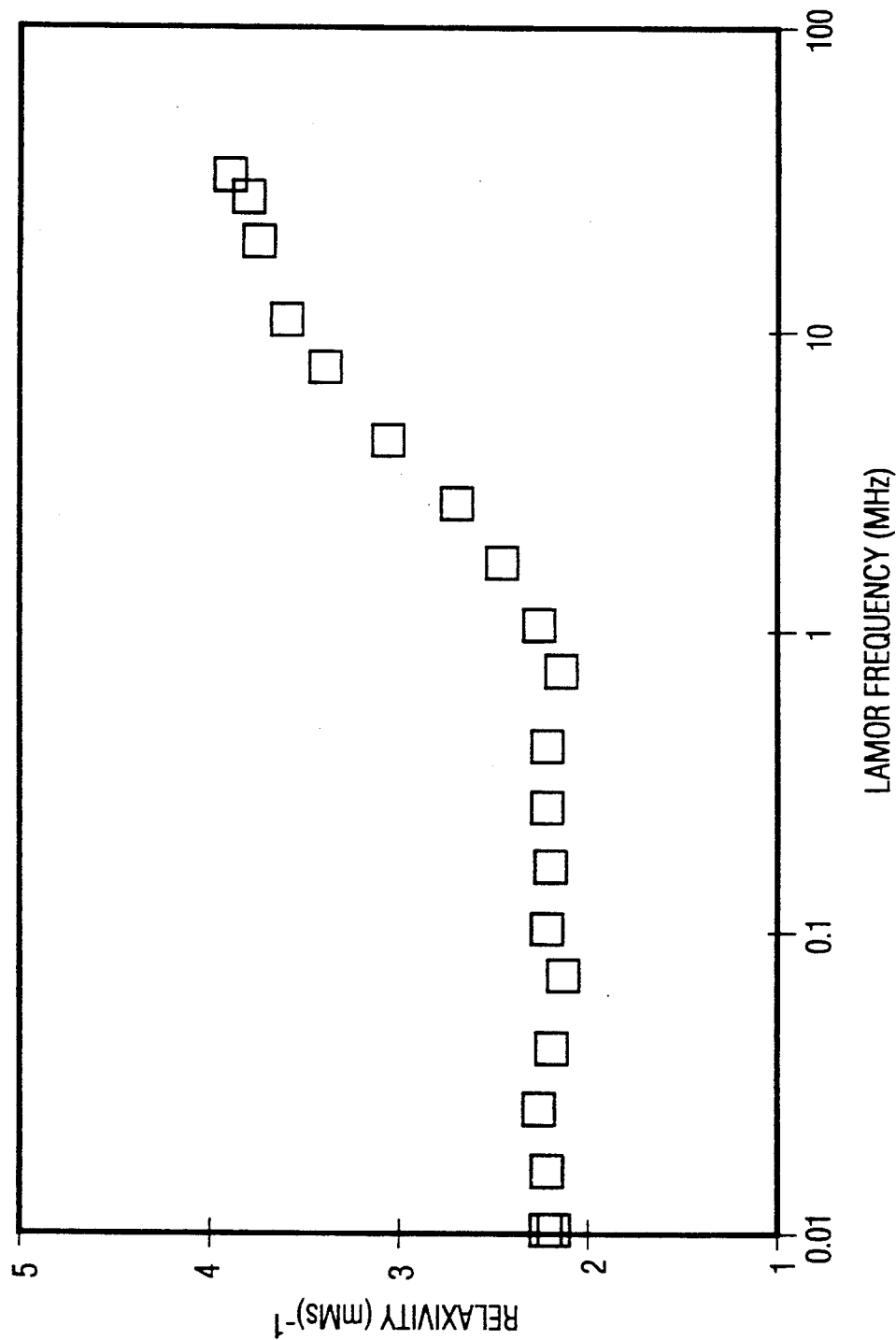
FIG. 1 is a graph of the relaxivity vs. frequency of the compound of formula III where $R_2$ is H, Y is Mn and X is Cl$^-$.

The results of relaxivity tests of the title compound are shown in FIG. 1. The relaxivity vs. frequency profile is similar to those of the Koenig et al reference cited supra. As can be seen from FIG. 1, the relaxivity is between 2 and 5 (mMs) at frequencies between 0.01 and 100 MHz.

C. Manganese(III)5,10,15,20-tetrakis[[4-carboxylic acid-(1,3-dihydroxyisopropyl)-amide]phenyl]porphyrin chloride The title B compound (0.39 g; $4.39 \times 10^{-4}$ moles) was dissolved in 200 mL spectral grade dimethylformamide. Thionyl chloride 0.35 mL ($4.8 \times 10^{-3}$ moles) was added slowly with stirring. The reaction mixture was then stirred for 3 hours under nitrogen or argon sparge. The dimethylformamide was removed under reduced pressure. The manganese acid-chloride porphyrin intermediate was then dried overnight under high vacuum.

This material was subsequently dissolved in 200 mL of methanol which was freshly distilled from sodium. A solution of 0.16 g 2-amino-1, 3-propanediol ("serinol", $1.8 \times 10^{-3}$ moles) in freshly distilled methanol was added slowly with stirring. Again the reaction flask was kept under a nitrogen or argon flow. The reaction was stopped and the methanol removed by evaporation. The solid was then dried overnight under high vacuum. This crude material was purified by passing aliquots down a Sephadex LH-20 column using a 50:50 methanol:water mixture as eluent.

Yield: 0.24 g; 47%.

Formulation: Managanese(III)5,10,15,20-tetrakis[[4-carboxylic acid-(1,3-dihydroxyisopropyl)amide]-phenyl]-porphyrin>chloride.$2H_2O.C_{60}H_{60}N_8O_{14}$ MnCl Proposed: %C 59.68, %H 5.01, %N 9.28, %Mn 4.55

Found: %C 59.88, %H 5.22, %N 8.82, %MN 4.69

UV-vis, nm ($\epsilon$in $(M \times 10^3 cm)^{-1}$), 598 (8.89); 566 (11.1); 513 (7.57); 468 (84.2); 401 (53.2); 381 (53.0).

Figure 2:
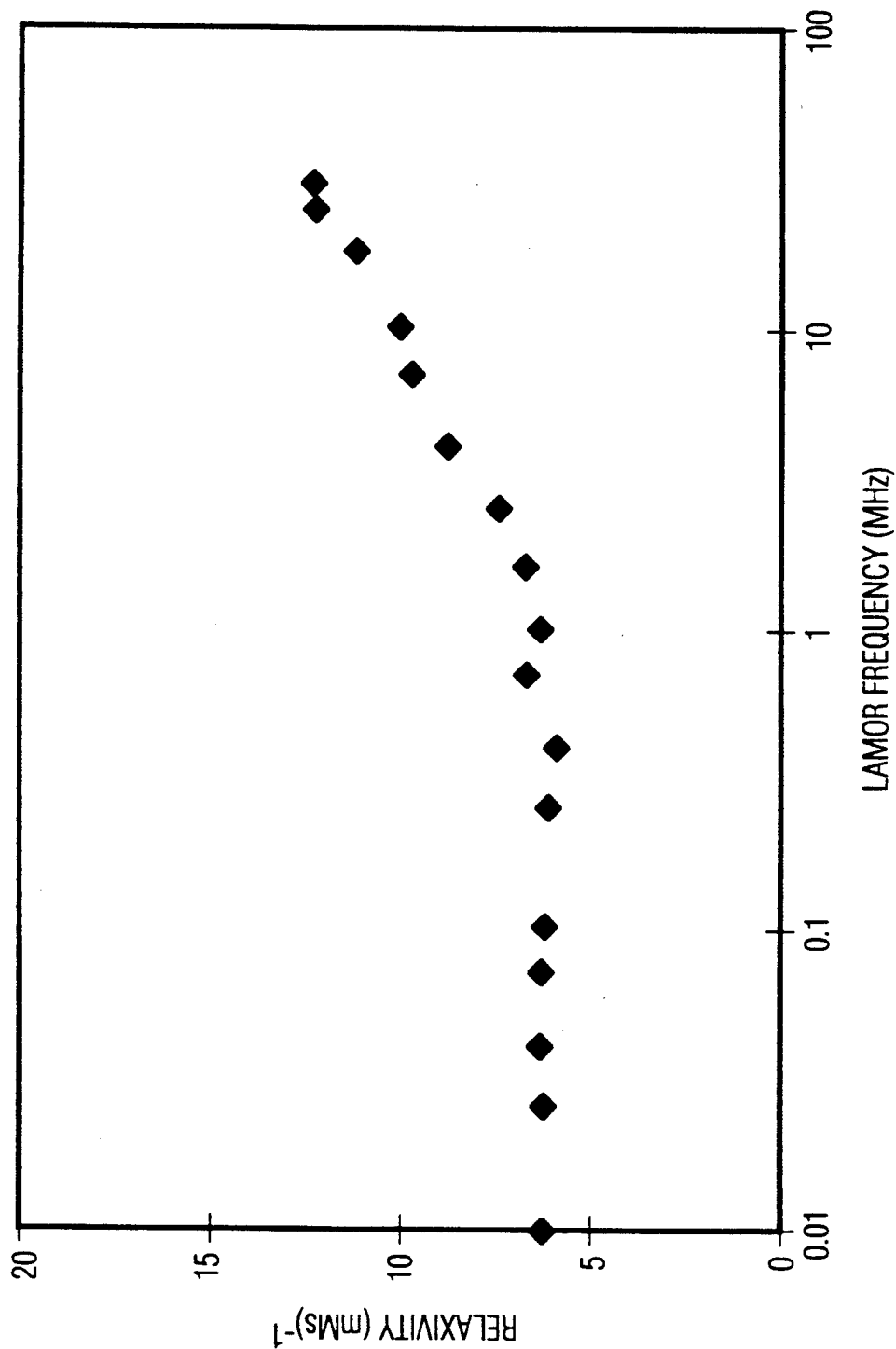
FIG. 2 is a graph of the relaxivity vs. frequency of the compound of formula I where R is

The results of relaxivity tests of the title compound are shown in FIG. 2. The relaxivity vs. frequency profile is similar to those of the Koenig et al reference cited supra and similar to FIG. 1. However, the magnitude of the relaxivity is greater than for the compound of Example 1B. More specifically, the relaxivity is between 5 and 15 $(mMs)^{-1}$ at frequencies between 0.01 and 40 MHz.

EXAMPLE 2

Manganese(III)5,10,15,20-tetrakis[[4-carboxylic acid-(1,3-dihydroxyisopropyl)amide]phenyl]porphyrin]chloride

A. 5,10,15,20-Tetrakis[4-carboxylic acid(1,3-dihydroxyisopropyl)amide]phenyl]porphyrin The title A compound of Example 1 (0.26 g, $3.29 \times 10^{-4}$ moles) was reacted with 0.25 mL thionyl chloride ($3.43 \times 10^{-3}$ moles) in 250 mL spectral grade dimethylformamide. This mixture was stirred at room temperature under a slow flow of nitrogen for 3 hours to form the acid-chloride of the porphyrin. The dimethylformamide was then removed under reduced pressure The remaining green solid was dried overnight under high vacuum at room temperature.

The acid-chloride porphyrin intermediate was then dissolved in 250 mL methanol which had been freshly distilled from sodium metal. Subsequently, 0.12 g 2-amino-1,3-propanediol ("serinol", $1.32 \times 10^{-3}$ moles) was dissolved in freshly distilled methanol (ca. 10 mL) and added to the acid chloride solution. The reaction mixture was stirred at room temperature for 1.5 hours under a slow flow of nitrogen, after which the methanol was removed under reduced pressure. The resulting crude solid was dried overnight under high vacuum. The material was then purified by passing aliquots down a Sephadex LH-20 column using a 50:50 methanol:water mixture as eluent.

Yield: 0.09 g; 25%

Formulation: 5,10,15,20-Tetrakis[[4-carboxylic acid-(1,3-dihydroxyisopropyl)amide]phenyl]porphyrin $3CH_3OH.5H_2O.C_{63} H_{80}N_8O_{20}$ Proposed: %C 59.61, %H 6.35, %N 8.83.

Found: %C 59.89, %H 5.47, %N 8.68.

$^1H$-NMR ($D_2O$, 300 MHz) $\delta$3.24 (s, 4H), 3.55 (m, 16H), 7.28 (s, 8H), 8.06 (s, 8H), 8.55 (br, 8H) ppm. $^{13}C$ DEPT NMR ($D_2O$, 300 MHz) % 56.3, 60.9, 129.6, 137.5 ppm.

B. Manganese(III)5,10,15,20-tetrakis[[4-carboxylic acid-(1,3-dihydroxyisopropyl)amide]phenyl]porphyrin chloride The title A compound (0.060 g, $5.54 \times 10^{-5}$ moles) was dissolved in dimethylformamide, and subsequently 0.021 g $MnCl_2.4H_2O$ ($1.06 \times 10^{-4}$ moles) was added with stirring. This mixture was then refluxed for a period of 18 hours. The dimethylformamide was removed by evaporation under reduced pressure.

This crude porphyrin mixture was purified via column chromatography, using Sephadex LH-20 and employing a 50:50 methanol:water solvent mixture. Purification of the mixture isolated two bands: a dark brown band (the desired manganese porphyrin) and a second red band (the unmetallated porphyrin starting material). The individual bands were independently recrystallized from methanol/diethyl ether. Yield of the title compound: 0.018 g; 27%.

Formulation: Manganese(III)5,10,15,20-tetrakis[[4-carboxylicacid-(1,3dihydroxyisopropyl)amide]phenyl]porphyrin chloride.2H$_2$O.C$_{60}$H$_{60}$N$_8$O$_{14}$ MnCl Proposed: %C 59.68, %H 5.01, %N 9.28, %Mn 4.55.
Found: %C 59.88, %H 5.22, %N 8.82, %Mn 4.69

UV-vis, nm ($\epsilon$in (M×10$^3$ cm)$^{-1}$), 598 (8.89); 566 (11.1); 513 (7.57); 468 (84.2); 401 (53.2); 381 (53.0).

EXAMPLE 3

Manganese(III)5,10,15,20-tetrakis[[4-carboxylic acid-(2,3-dihydroxypropyl)amide]phenyl]porphyrin chloride The title B compound from Example 1 (0.25 g; 2.84×10$^{-4}$ moles) was reacted with 0.25 mL thionyl chloride (3.41×10 a moles, 12 molar excess) in 200 mL spectral grade dimethylformamide. The reaction was carried out under a slow flow of argon, with stirring and gentle heating (ca, 50° C.), for 2 hours. The dimethylformamide was removed under reduced pressure, and the resulting solid intermediate was dried on the vacuum line.

The acid-chloride metalloporphyrin was then dissolved in 200 mL methanol (freshly distilled from sodium metal) and stirred under a slow flow of argon. Subsequently, 0.13 g 3-amino-1,2-propanediol ("isoserinol", 1.42×10$^{-3}$ moles, 5 molar excess) was dissolved in a minimum amount of freshly distilled methanol and added to the reaction. The reaction was continued with gentle heating (ca. 40° C.) for 2 hours, after which the methanol was removed under reduced pressure and the resulting crude solid dried on the vacuum line. Purification was accomplished via a Sephadex LH-20 column employing a 50:50 methanol:water solvent system. The metalloporphyrin eluted as a single dark band, from which the front and trailing fractions were discarded. The band was reduced to dryness and recrystallized from methanol/diethyl ether to yield dark crystals.

Yield: 0.18 g; 54%.

Formulation: Manganese(III)5,10,15,20-tetrakis[[4-carboxylic acid-(2,3-dihydroxypropyl)amide]phenyl]porphyrinchloride. 2CH$_3$OH.2H$_2$O. C$_{62}$H$_{68}$N$_8$O$_{16}$McCl Proposed: %C 58.56, %H 5.39, %N 8.81
Found: %C 58.69, %H 5.12, %N 8.51

UV-vis, nm ($\epsilon$in (M×10$^{\cdot}$cm)$^{-1}$), 599 (6.06); 564 (7.44); 513 (7.32); 468 (31.4); 401 (26.4); 379 (27.2)

The results of relaxivity tests of the title compound are shown in FIG. 3. The magnitude of the relaxivity (effectiveness) is unexpectedly high, being >20(mMs)$^{-1}$ at frequencies between 10 and 40 MHz.

What is claimed is:

1. A compound of formula

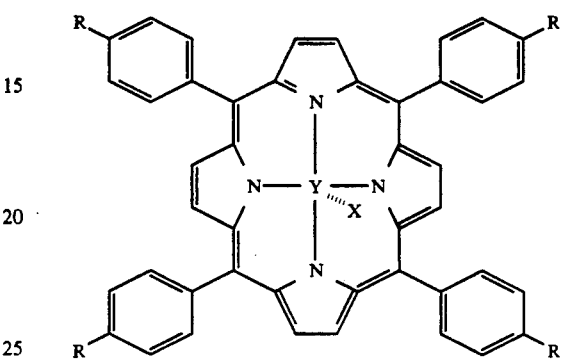

where Y is a transition metal selected from the group consisting of Fe$^{III}$, Cr$^{III}$ and Mn$^{III}$, X is a biologically well-tolerated complexing anion selected from the group consisting of Cl—, CF$_3$SO$_3$—and CF$_3$COO—and R is a nonionic water solubilizing moiety selected from the group consisting of

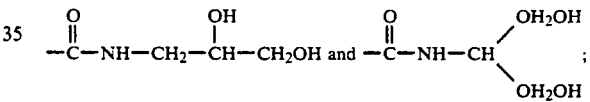

or pharmaceutically acceptable salts thereof.

2. The compound of claim 1 having the name Manganese(III)5,10,15,20-tetrakis[[4-carboxylic acid-1-3-dihydroxyisopropyl)amide]phenyl]porphyrin chloride.

3. The compound of claim 1 having the name Manganese(III)5,10,15,20-tetrakis[[4-carboxylic acid-(2-3-dihydroxypropyl)amide]phenyl]porphyrin chloride.

* * * * *